(12) United States Patent
Abe et al.

(10) Patent No.: US 6,858,161 B2
(45) Date of Patent: Feb. 22, 2005

(54) METHOD FOR PURIFYING ELECTRONIC ITEM MATERIAL

(75) Inventors: Katsumi Abe, Ibaraki (JP); Tomonori Nishimura, Ibaraki (JP); Takanobu Watanabe, Ibaraki (JP); Susumu Suzuka, Ibaraki (JP)

(73) Assignee: Hodogaya Chemical Co., Ltd., Kawasaki (JP)

( * ) Notice: Subject to any disclaimer, the term of this patent is extended or adjusted under 35 U.S.C. 154(b) by 97 days.

(21) Appl. No.: 09/893,684

(22) Filed: Jun. 29, 2001

(65) Prior Publication Data

US 2003/0050489 A1 Mar. 13, 2003

(30) Foreign Application Priority Data

Jun. 30, 2000 (JP) .......................................... 2000-199334

(51) Int. Cl.$^7$ ................................................. H01B 1/12
(52) U.S. Cl. ................. 252/500; 252/501.1; 210/500.1; 423/DIG. 14
(58) Field of Search ............................. 252/500, 501.1; 210/500.1; 423/DIG. 14

(56) References Cited

U.S. PATENT DOCUMENTS 5,206,103 A * 4/1993 Stolka et al. ................. 430/59

FOREIGN PATENT DOCUMENTS

| JP | 39-11546 | 6/1964 |
|---|---|---|
| JP | 54-58445 | 5/1979 |
| JP | 55-46760 | 4/1980 |
| JP | 55-52063 | 4/1980 |
| JP | 55-154955 | 12/1980 |
| JP | 55-156954 | 12/1980 |
| JP | 56-81850 | 7/1981 |
| JP | 57-73075 | 5/1982 |
| JP | 57-195254 | 11/1982 |
| JP | 57-205437 | 12/1982 |
| JP | 58-32372 | 2/1983 |
| JP | 58-198043 | 11/1983 |
| JP | 60-34099 | 2/1985 |
| JP | 60-233156 | 11/1985 |
| JP | 1-149055 | 6/1989 |
| JP | 2-190863 | 7/1990 |
| JP | 3-39306 | 2/1991 |
| JP | 3-253861 | 11/1991 |
| JP | 3-285960 | 12/1991 |
| JP | 4-310962 | 11/1992 |
| JP | 6-148915 | 5/1994 |
| JP | 6-214412 | 8/1994 |
| JP | 6-317918 | 11/1994 |
| JP | 7-13741 | 1/1995 |
| JP | 7-56365 | * 3/1995 |
| JP | 7-84390 | 3/1995 |
| JP | 7-126226 | 5/1995 |
| JP | 7-188130 | 7/1995 |
| JP | 7-281462 | 10/1995 |
| JP | 2529299 | 8/1996 |
| JP | 8-211636 | 8/1996 |
| JP | 2539641 | 10/1996 |
| JP | 2552695 | 11/1996 |
| JP | 8-295655 | 11/1996 |
| JP | 9-208549 | 8/1997 |
| JP | 9-216877 | 8/1997 |
| JP | 9-258465 | 10/1997 |
| JP | 9-328456 | 12/1997 |
| JP | 10-31319 | 2/1998 |
| JP | 10-148952 | 6/1998 |
| JP | 11-76763 | * 3/1999 |
| JP | 11-84694 | * 3/1999 |

* cited by examiner

*Primary Examiner*—Mark Kopec
(74) *Attorney, Agent, or Firm*—Oblon, Spivak, McClelland, Maier & Neustadt, P.C.

(57) ABSTRACT

A method for purifying an electronic item material, which comprises dissolving an electronic item material or its intermediate product in an organic solvent and having the solution contacted with activated clay at a temperature of 65° C. to 200° C.

13 Claims, No Drawings ately, a material having a satisfactory level of properties could not be obtained. On the other hand, a purification method by sublimation to obtain a high purity product achieved only a low yield, and raised industrially unfavorable problems.

METHOD FOR PURIFYING ELECTRONIC ITEM MATERIAL

BACKGROUND OF THE INVENTION

1. Field of the Invention

The present invention relates to a method for purifying an electronic item material or its intermediate product, such as a charge-transporting material for an electrophotographic photoconductor used in an electrophotographic system type copying machine, printer, facsimile or the like.

2. Discussion of Background

A material used as a charge-transporting material is required to be a material having a high purity in order to provide stable performances from an initial stage to a long period use when it is used for an electrophotographic photoconductor.

Generally, in order to provide these performances, it is essential to purify a produced crude product. As a purification method by an adsorbent, JP-A-60-233156 discloses a method comprising a combination of activated clay and activated carbon, and JP-A-4-310962 discloses a purification method comprising purifying with activated clay and then purifying with active silica. They are a method comprising a combination of several kinds of adsorbents, but JP-A-7-56365 discloses a method comprising repeating a purification treatment operation at least 2 times to improve a purification effect. These methods raise a problem of increasing a starting material cost by using many kinds of adsorbents and a problem of increasing a cost by repeating the same treatment operation. Also, a material having satisfactory electric properties required for an electrophotographic photoconductor could be sometimes obtained by treatment with an adsorbent such as activated carbon, activated clay or the like, but in many cases, a material having a satisfactory level of properties could not be obtained. On the other hand, a purification method by sublimation to obtain a high purity product achieved only a low yield, and raised industrially unfavorable problems.

SUMMARY OF THE INVENTION

An object of the present invention is to provide a method for purifying a charge-transporting material, enabling a mass production of a charge-transporting material for an electrophotographic photoconductor, which has satisfactory electric characteristics in respect of a residual potential, a sensitivity and the like, and does not contain such an impurity as to deteriorate electric characteristics, in order to produce an electrophotographic photoconductor, the properties of which do not vary even in a fatigued state, and further, an object of the present invention is to provide a method for purifying an electronic item material in the same viewpoint.

The present inventors have intensively studied to research for a purification method enabling a mass production of a charge-transporting material having satisfactory electric properties, and have discovered that electric properties of a charge-transporting material or an electronic item material can be greatly improved by carrying out treatment with activated clay under a predetermined temperature condition. The present invention has been accomplished on the basis of this discovery. That is, the present invention provides a method for purifying an electronic item material, which comprises dissolving an electronic item material or its intermediate product in an organic solvent and having the solution contacted with activated clay at a temperature of 65° C. to 200° C.

Also, the present invention provides a method for purifying an electronic item material which comprises dissolving an electronic item material in an organic solvent and having the solution contacted with activated clay at a temperature of 80° C. to 130° C.

Particularly, the electronic item material of the present invention includes an electrophotographic photoconductor, an organic electroluminescent device, a charge-transporting material or the like.

Further, the present invention provides an electronic item material or its intermediate product purified by a purification method which comprises dissolving an electronic item material or its intermediate product in an organic solvent and having the solution contacted with activated clay at a temperature of 65° C. to 200° C., preferably 80° C. to 130° C.

DETAILED DESCRIPTION OF THE INVENTION

When purifying with activated clay, it is possible to remove a part of impurities even by a general treatment method, but it can not be expected to achieve a largely improved effect even by treating for a longer time. At a temperature in the vicinity of room temperature, it is impossible to expect an effect improved more than the initial effect even by prolonging a contact time longer, increasing the number of repeating contact times or increasing the amount of activated clay. However, when the treatment is carried out at a temperature of at least 65° C., preferably at least 80° C., the improvement of performances which could not be achieved at a temperature in the vicinity of room temperature can be easily and remarkably achieved.

Examples of a charge-transporting material of the present invention include arylamine derivatives, benzidine derivatives, hydrazone derivatives, stilbene derivatives, and the like. Particular examples include arylamine derivatives (disclosed in JP-A-57-195254, JP-A-2-190863, JP-A-3-285960, JP-A-6-214412, JP-A-6-317918, JP-A-7-84390, JP-A-7-281462, and JP-A-9-258465), benzidine derivatives (disclosed in JP-A-54-58445, JP-A-6-148915, JP-A-6-214412, JP-A-7-126226, JP-A-7-188130, JP-B-39-11546, JP-B-58-32372, and U.S. Pat. No. 2,539,641), hydrazone derivatives (disclosed in JP-A-55-46760, JP-A-55-154955, JP-A-55-156954, JP-A-55-52063, JP-A-56-81850, JP-A-10-31319, and JP-B-60-34099), stilbene derivatives (disclosed in JP-A-57-73075, JP-A-57-205437, JP-A-58-198043, JP-A-8-211636, JP-A-9-208549, JP-A-9-216877, JP-A-9-328456, JP-A-10-148952, and JP-B-3-39306), styryl derivatives (disclosed in JP-A-7-281462), distilbene derivatives (disclosed in JP-A-3-253861, JP-B-7-13741, and U.S. Pat. No. 2,552,695), tristyryl derivatives (disclosed in JP-A-8-295655), diethyl aromatic compounds (disclosed in U.S. Pat. No. 2,529,299), butadiene derivatives (disclosed in JP-A-1-149055), and the like. Among them, the purification method of the present invention is effective particularly for benzidine derivatives. The charge-transporting material is used mainly as an electrophotographic photoconductor, and also as an organic electroluminescent device. If a specific impurity is present in these uses, it gives a severe bad influence on performances of an electrophotographic photoconductor even when it is present only in quite a minor small amount. It is a favorable feature of the purification method of the present invention that can precisely remove such a specific impurity. In the past, activated clay was used to carry out decoloration or to remove impurities of petroleum products, but the purification method of the present invention is not limited to the purification of a charge-transporting material and is also very effective for purifying an electronic item material to remove a specific impurity, the presence of which gives a severe bad influence on electric functions and electronic functions even in quite a minor small amount. Also, by applying the purification method of the present invention to a specific intermediate, it is possible to certainly improve electric properties of a final product.

Examples of activated clay to be used include activated clay activated by sulfuric acid-treating acidic clay and natural minerals such as kaolin, bentonite, pearlite, bauxite, acidic clay or the like. Active alumina and silica gel containing the main elements of these compounds are also usable. Preferable examples of activated clay include activated "active clay", and those commercially available from Nihon Hakudo K. K. (tradename: Activated Clay), mizusawa Industrial Chemicals, Ltd. (tradename: Galleon Earth, Galleonite or the like), and the like are usable.

Generally, preferably usable powdery activated clay has properties including a water content of at most 12% or at most 5%, a powder size of at least 85% pass through 200 mesh, a free acid amount of at most 2 mgKOH/g, and an apparent specific gravity of 0.45 to 0.85. Also, preferably usable particulate activated clay has properties including a water content of at most 12% or at most 5%, a powder size of 15 to 30 mesh, 30 to 60 mesh and 8 to 16 mesh, a free acid of at most 2 mgKOH/g, and an apparent specific gravity of 0.55 to 0.75. Further, preferably usable activated clay has a surface area of at least 150 m$^2$/g and an acidity of 10 to 30 m.e./100 g, and contains 70 to 85% of SiO$_2$ and 6 to 15% of Al$_2$O$_3$ as the main components.

Activated clay is used in an amount of at least 10% by weight, preferably 20 to 100% by weight, to the weight of an electronic item material. Treatment is carried out by dissolving an electronic item material in an organic solvent and having the resultant solution contacted with activate clay. After contacting, the solution and the clay are separated from each other by a filtrating machine.

Treatment temperature is usually in a range of 65 to 200° C., preferably 80 to 130° C. Contact time can be optionally selected, but is preferably at least 10 minutes, more preferably 20 to 200 minutes.

Any organic solvent is usable so long as it dissolves a charge-transporting material, but is preferably aliphatic and aromatic hydrocarbons. Particularly preferable examples include toluene, o-xylene, m-xylene, p-xylene, o-cymene, m-cymene, p-cymene, anisole, n-hexane, n-heptane, n-octane, n-decane, n-dodecane, 2,3-dimethylhexane, 2-methylheptane, 2-methylhexane, 3-methylhexane, ethylxylene, ethyltoluene, ethylanisole, dimethylheptane, and the like, and they may be used alone or in a mixture.

Filtration after contacting is efficiently carried out preferably at such a high temperature as to be acceptable to a solvent and an equipment used, but the filtration may be carried out even after cooling.

In the present invention, activated clay may be added at any stage before or after dissolving an electronic item material in an organic solvent. The total amount of the activated clay may be added by one time or may be added dividedly by several times.

In the case of a charge-transporting material, contact treatment with activated clay is carried out by dissolving a charge-transporting material in an organic solvent, adding activated clay to the resultant solution and stirring the mixture at a temperature in a range of 65 to 200° C. for at least 20 minutes to have the charge-transporting material fully contacted with the activated clay. After contacting, the activated carbon was removed by filtration. The charge-transporting material obtained by such a purification method has satisfactory electric properties.

EXAMPLES

The present invention will be concretely described with reference to the following Examples.

Example 1

Benzidine compound (charge-transporting material No. 1) as a charge-transporting material

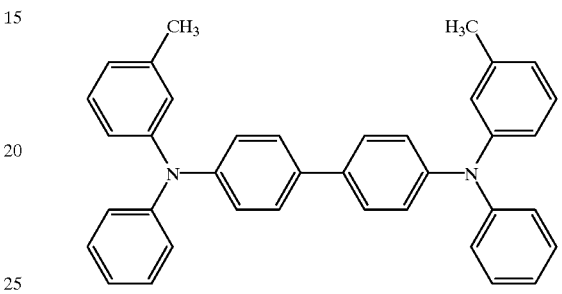

10 g of the above charge-transporting material was dissolved in 60 g of toluene, and 10 g of activated clay "Kyou" (NIPPON KASSEIHAKUDO CO., LTD.) was added thereto, and the resultant mixture was stirred at 100° C. for 1 hour, and the mixture was then filtrated, and 240 g of methanol was dropwise added to the toluene solution to precipitate a crystal. The crystal was separated by filtration, and was then dried to obtain 8.1 g of a treated product (yield 81%). The product had a purity of 99.7% according to analysis by a high performance liquid chromatography (HPLC-6A, manufactured by Shimadzu Corporation).

A photoconductor was prepared by using the above obtained treated product in the following manner, and its electrophotographic performances were evaluated. 2.5 parts of alcohol-soluble nylon (Amilan CM-8000, manufactured by Toray Industries, Inc.) was added to 100 parts of a 1:1 (W/W) mixture solution of methanol/n-butanol to be fully dissolved therein. The resultant solution was coated on an aluminum surface of an aluminum-vapordeposited PET film as an electroconductive substrate by a wire bar, and was dried at 110° C. under normal pressure for 10 minutes to form an undercoat layer having a thickness of 0.2 μm.

χ type metal free phthalocyanine (charge-generating material No. 1) as a charge-generating material

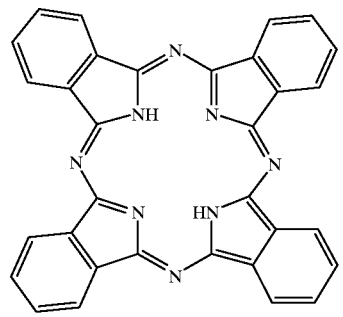

1.5 parts of the above charge-generating material was added to 50 parts of a 3% cyclohexanone solution of polyvinyl butyral resin (Eslex BL-S, manufactured by Sekisui Chemical Co., Ltd.), and the resultant mixture was subjected to milling in a pot mill for 24 hours. The dispersion thus obtained was coated on the above undercoat layer by a wire bar, and was dried at 110° C. under normal pressure for 30 minutes to form a charge-generating layer having a thickness of 0.5 μm.

On the other hand, 1.5 parts of the treated product of charge-transporting material No. 1 as a charge-transporting material was added to 12 parts of a 10% toluene solution of polycarbonate resin (IUPILON Z, manufactured by Mitsubishi Engineering Plastic K. K.), and was completely dissolved therein by applying ultrasonic wave. The solution thus obtained was coated on the above charge-generating layer by a wire bar, and was dried at 110° C. under normal pressure for 30 minutes and further dried under reduced pressure for 2 hours to form a charge-transporting layer having a thickness of 22 μm, thus producing a photoconductor.

Electrophotographic performances of the photoconductor thus produced were evaluated by an electrostatic copying paper tester (tradename "EPA-8100" manufactured by Kawaguchi Denki Seisakusho K. K.). The photoconductor was subjected to −6 kv corona discharge in the dark to measure a charge potential V0. The photoconductor was then subjected to exposure with 780 nm monocolor of 1.0 μW/cm$^2$, and a half decay exposure amount E1/2 (μJ/cm$^2$) and a residual potential Vr after light irradiation for 5 seconds were determined. The results are shown in the following Table 1-1.

Comparative Example 1

10 g of the benzidine compound (charge-transporting material No. 1) was dissolved in 60 g of toluene, and 10 g of activated clay "Kyou" was added thereto, and the resultant mixture was stirred at 50° C. for 1 hour, and the mixture was subjected to filtration, and 240 g of methanol was dropwise added to the above obtained toluene solution to precipitate a crystal. The crystal thus precipitated was separated by filtration, and was dried to obtain 8.1 g of a treated product (yield 81%). The treated product thus obtained had a purity of 99.6% according to analysis by a high performance liquid chromatography (HPLC-6A, manufactured by Shimadzu Corporation). A photoconductor was prepared by using the above obtained treated product in the same manner as in Example 1, and its electrophotographic performances were evaluated in the same manner as in Example 1.

Example 2

The following benzidine compound (charge-transporting material No. 2) was used in place of the charge-transporting material No. 1 used in Example 1, and the same procedure as in Example 1 was repeated to obtain 8.0 g of a treated product (yield 80%).

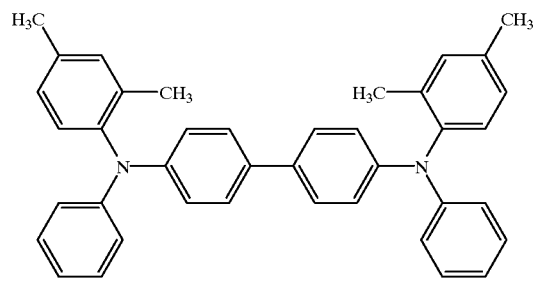

The treated product thus obtained had a purity of 99.9% according to purity analysis carried out in the same manner as above.

By using the treated product thus obtained, a photoconductor was prepared and its electrophotographic performances were evaluated in the same manner as in Example 1

τ type metal free phthalocyanine (charge-generating material No. 2) was used as a charge-generating material in place of the charge-generating material No. 1 used in Example 1.

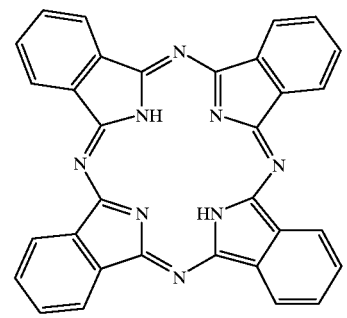

Comparative Example 2

The benzidine compound (charge-transporting material No. 2) was treated in the same manner as in Comparative Example 1 to obtain 8.1 g of a treated product (yield 81%). The treated product thus obtained had a purity of 99.8% according to purity analysis carried out in the same manner as above.

A photoconductor was prepared by using the treated product thus obtained in the same manner as in Example 2, and its electrophotographic performances were evaluated in the same manner as above.

Example 3

The following benzidine compound (charge-transporting material No. 3) was used in place of the charge-transporting material No. 1 used in Example 1, and the same procedure as in Example 1 was repeated to obtain 8.3 g of a treated product (yield 83%).

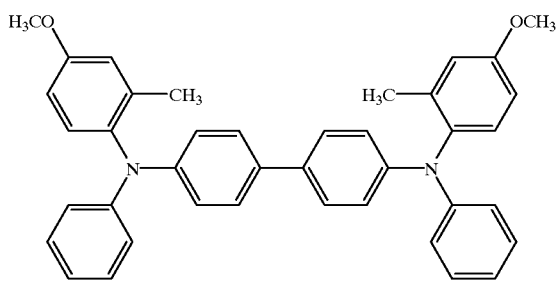

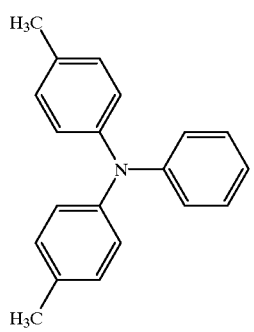

The treated product thus obtained had a purity of 99.7% according to purity analysis carried out in the same manner as above.

A photoconductor was prepared by using the above obtained treated product in the same manner as in Example 1, and its electrophotographic performances were evaluated in the same manner as above.

α type oxotitanyl phthalocyanine (charge-generating material No. 3) was used as a charge-generating material in place of the charge-generating material No. 1 used in Example 1.

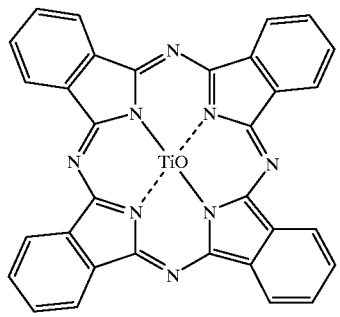

Comparative Example 3

The bendizine compound (charge-transporting material No. 3) was treated in the same manner as in Comparative Example 1 to obtain 8.2 g of a treated product (yield 82%). The treated product thus obtained had a purity of 99.5% according to purity analysis carried out in the same manner as above.

A photoconductor was prepared by using the treated product thus obtained in the same manner as in Example 3, and its electrophotographic performances were evaluated in the same manner as above.

Example 4

The following amine compound (charge-transporting material No. 4) was used in place of the charge-transporting material No. 1 used in Example 1, and the same procedure as in Example 1 was repeated to obtain 8.0 g of a treated product (yield 80%).

The treated product thus obtained had a purity of 99.9% according to purity analysis carried out in the same manner as above.

A photoconductor was prepared by using the above obtained treated product in the same manner as in Example 3, and its electrophotographic performances were evaluated in the same manner as above.

Comparative Example 4

The amine compound (charge-transporting material No. 4) was treated in the same manner as in Comparative Example 1 to obtain 8.1 g of a treated product (yield 81%). The treated product thus obtained had a purity of 99.8% according to purity analysis carried out in the same manner as above.

A photoconductor was prepared by using the above obtained treated product in the same manner as in Example 3, and its electrophotographic performances were evaluated in the same manner as above.

Example 5

The following amine compound (charge-transporting material No. 5) was used in place of the charge-transporting material No. 1 used in Example 1, and was treated in the same manner as in Example 1 to obtain 7.8 g of a treated product (yield 78%).

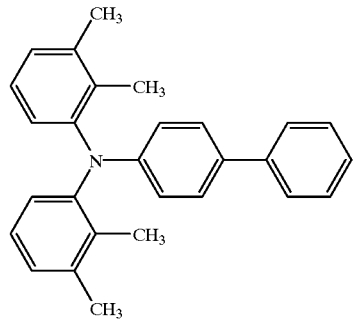

The treated product thus obtained had a purity of 99.7% according to purity analysis carried out in the same manner as above.

A photoconductor was prepared by using the above obtained treated product in the same manner as in Example 3, and its electrophotographic performances were evaluated in the same manner as above.

Comparative Example 5

The amine compound (charge-transporting material No. 5) was treated in the same manner as in Comparative Example 1 to obtain 7.8 g of a treated product (yield 78%). The treated product thus obtained had a purity of 99.6% according to purity analysis carried out in the same manner as above.

A photoconductor was prepared by using the above obtained treated product in the same manner as in Example 3, and its electrophotographic performances were evaluated in the same manner as above.

Example 6

The following amine compound (charge-transporting material No. 6) was used in place of the charge-transporting material No. 1 used in Example 1, and was treated in the same manner as in Example 1 to obtain 7.6 g of a treated product (yield 76%).

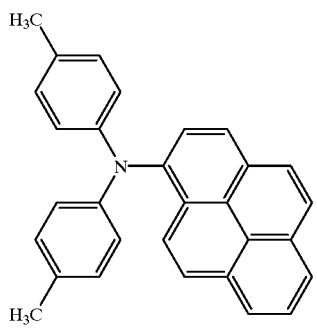

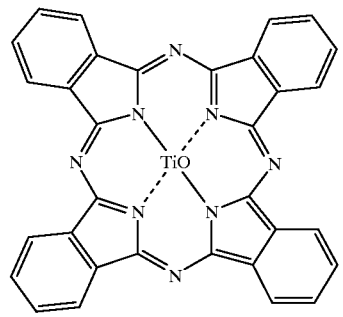

Comparative Example 6

The amine compound (charge-transporting material No. 6) was treated in the same manner as in Comparative Example 1 to obtain 7.5 g of a treated product (yield 75%). The treated product thus obtained had a purity of 99.6% according to purity analysis carried out in the same manner as above.

A photoconductor was prepared by using the above obtained treated product in the same manner as in Example 6, and its electrophotographic performances were evaluated in the same manner as above.

Example 7

Benzidine compound (charge-transporting material No. 7) as a charge-transporting material

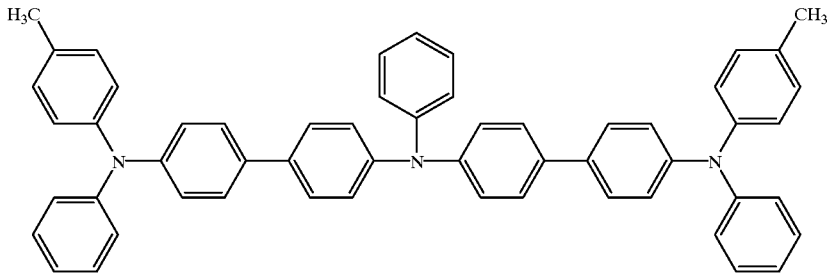

The treated product thus obtained had a purity of 99.8% according to purity analysis carried out in the same manner as above.

A photoconductor was prepared by using the above obtained treated product in the same manner as in Example 1, and its electrophotographic performances were evaluated in the same manner as above.

The following y type oxotitanyl phthalocyanine (charge-generating material No. 4) was used as a charge-generating material in place of the charge-generating material No. 1 used in Example 1.

10 g of the above benzidine compound was dissolved in 70 g of p-xylene, and 10 g of activated clay T (manufactured by NIPPON KASSEIHAKUDO CO., LTD.) was added thereto, and the mixture was stirred at 130° C. for 1 hour, and the mixture was subjected to separation by filtration, and 300 g of methanol was dropwise added to the above obtained toluene solution to precipitate a crystal. The crystal thus precipitated was separated by filtration, and was dried to obtain 9.0 g of a treated product (yield 90%). The treated product thus obtained had a purity of 99.7% according to purity analysis carried out by a high performance liquid chromatograph (HPLC-6A, manufactured by Shimadzu Corporation).

A photoconductor was prepared by using the above obtained treated product in the following manner, and its electrophotographic performances were evaluated in the following manner.

2.5 parts of alcohol-soluble nylon (Amilan CM-8000, manufactured by Toray Industries, Inc.) was added to 100 parts of a 1:1 (w/W) mixture solution of methanol/n-butanol, and was completely dissolved therein. The solution thus obtained was coated on an aluminum surface of an aluminum-vapordeposited PET film as an electroconductive substrate by a wire bar, and was dried at 110° C. under normal pressure for 10 minutes to form an undercoat layer having a thickness of 0.2 m.

On the other hand, 1.5 parts of χ type metal free phthalocyanine (charge-generating material No. 1) as a charge-generating material was added to 50 parts of a 3% cyclohexanone solution of polyvinyl butyral resin (Eslex BL-S, manufactured by Sekisui Chemical Co., Ltd.), and the resultant mixture was subjected to milling in a pot mill for 24 hours. The dispersion thus obtained was coated on the

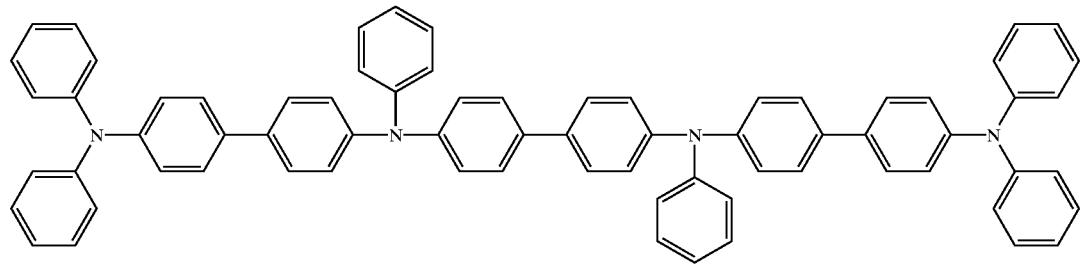

above undercoat layer by a wire bar, and was dried at 110° C. under normal pressure for 30 minutes to form a charge-generating layer having a thickness of 0.5 μm.

On the other hand, 1.5 parts of the above treated product as a charge-transporting material was added to 12 parts of a 10% toluene solution of polycarbonate resin (IUPILON Z, manufactured by Mitsubishi Engineering Plastic K. K.), and was completely dissolved therein by applying ultrasonic wave. The solution thus obtained was coated on the above charge-generating layer by a wire bar, and was dried at 110° C. under normal pressure for 30 minutes, and was further dried under reduced pressure for 2 hours to form a charge-transporting layer having a thickness of 22 μm, thus producing a photoconductor.

Electrophotographic performances of the above produced photoconductor were evaluated by using an electrostatic copying paper tester (tradename "EPA-8100" manufactured by Kawaguchi Denki Seisakusho K. K.). The photoconductor was subjected to corona discharge of −6 kV, and a charge potential V0 was measured at this time. The photoconductor was then exposed to 780 nm monocolor light of 1.0 μW/cm², and a half decay exposure amount E1/2 (μJ/cm²) and a residual potential Vr after light irradiation for 5 seconds were measured. The results are shown in the following Table 1-1.

Comparative Example 7

10 g of the benzidine compound (charge-transporting material No. 7) was dissolved in 70 g of p-xylene, and 10 g of activated clay T was added thereto, and the resultant mixture was stirred at 50° C. for 1 hour, and was then subjected to separation by filtration, and 300 g of methanol was dropwise added to the above obtained toluene solution to precipitate a crystal. The crystal thus precipitated was separated by filtration, and was dried to obtain 8.9 g of a treated product (yield 89%). The treated product thus obtained had a purity of 99.6% according to purity analysis carried out by using a high performance liquid chromatography (HPLC-6A, manufactured by Shimadzu Corporation).

A photoconductor was prepared by using the above obtained treated product in the same manner as in Example 7, and its electrophotographic performances were evaluated in the same manner as above.

Example 8

The following benzidine compound (charge-transporting material No. 8) was used in place of the charge-transporting material No. 7 used in Example 7, and was treated in the same manner as in Example 7 to obtain 9.2 g of a treated product (yield 92%).

The treated product thus obtained had a purity of 99.8% according to purity analysis carried out in the same manner as above.

A photoconductor was prepared by using the above obtained treated product in the same manner as in Example 7, and its electrophotographic performances were evaluated in the same manner as above.

α type oxotitanyl phthalocyanine (charge-generating material No. 3) was used as a charge-generating material in place of the charge-generating material No. 1 used in Example 7.

Comparative Example 8

The benzidine compound (charge-transporting material No. 8) was treated in the same manner as in Comparative Example 7 to obtain 9.1 g of a treated product (yield 91%). The above obtained treated product had a purity of 99.5% according to purity analysis carried out in the same manner as above.

A photoconductor was prepared by using the above obtained treated product in the same manner as in Example 7, and its electrophotographic performances were evaluated in the same manner as above.

Example 9

Amine compound (charge-transporting material No. 9) as a charge-transporting material

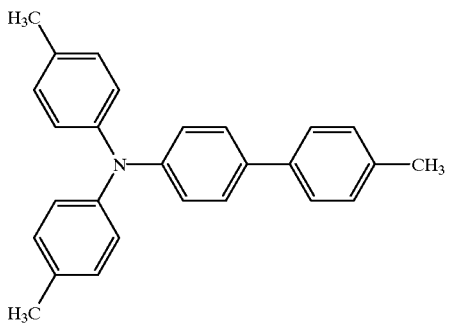

10 g of the above amine compound (charge-transporting material No. 9) was dissolved in 55 g of toluene, and 10 g of Galleon Earth $V_2$ (manufactured by Mizusawa Industrial Chemicals, Ltd.) was added thereto, and the resultant mixture was stirred at 90° C. for 1 hour, and was subjected to separation by filtration, and 250 g of methanol was dropwise added to the toluene solution to precipitate a crystal.

The crystal thus precipitated was separated by filtration, and was dried to obtain 8.6 g of a treated product (yield 86%). The treated product thus obtained had a purity of 99.5% according to purity analysis carried out by using a high performance liquid chromatography (HPLC-6A, manufactured by Shimadzu Corporation).

A photoconductor was prepared by using the above obtained treated product in the following manner, and its electrophotographic performances were evaluated in the following manner.

2.5 parts of alcohol-soluble nylon (Amilan CM-8000, manufactured by Toray Industries, Inc.) was added to 100 parts of a 1:1 (W/W) mixture solution of methanol/n-butanol, and was completely dissolved therein. The solution thus obtained was coated on an aluminum surface of an aluminum-vapordeposited PET film as an electroconductive substrate by a wire bar, and was dried at 110° C. under normal pressure for 10 minutes to form an undercoat layer having a thickness of 0.2 μm.

On the other hand, 1.5 parts of y type oxotitanyl phthalocyanine (charge-generating material No. 4) as a charge-generating material was added to 50 parts of a 3% cyclohexanone solution of polyvinyl butyral resin (Eslex BL-S, manufactured by Sekisui Chemical Co., Ltd.), and the resultant mixture was subjected to milling in a pot mill for 24 hours. The dispersion thus obtained was coated on the above obtained undercoat layer by a wire bar, and was dried at 110° C. under normal pressure for 30 minutes to form a charge-generating layer having a thickness of 0.5 μm.

On the other hand, 1.5 parts of the above treated product as a charge-transporting material was added to 12 parts of a 10% toluene solution of polycarbonate resin (IUPILON Z, manufactured by Mitsubishi Engineering Plastic K. K.), and was completely dissolved therein by applying ultrasonic wave. The solution thus obtained was coated on the above charge-generating layer by a wire bar, and was dried at 110° C. under normal pressure for 30 minutes and was further dried under reduced pressure for 2 hours to form a charge-transporting layer having a thickness of 22 μm, thus producing a photoconductor.

Electrophotographic performances of the above produced photoconductor were evaluated by using an electrostatic copying paper tester (tradename "EPA-8100" manufactured by Kawaguchi Denki Seisakusho K. K.). Corona discharge of −6 kV was applied to the photoconductor in the dark to measure a charge potential V0 at this time. The photoconductor was then exposed to 780 nm monocolor light of 1.0 μW/cm$^2$ to measure a half decay exposure amount E1/2 (μJ/cm$^2$) and a residual potential Vr after continuous irradiation with light for 5 seconds. The results are shown in the following Table 1-1.

Comparative Example 9

10 g of the amine compound (charge-transporting material No. 9) was dissolved in 55 g of toluene, and 10 g of Galleon Earth $V_2$ (manufactured by Mizusawa Industrial Chemicals, Ltd.) was added thereto, and the resultant mixture was stirred at 45° C. for 1 hour, and was subjected to separation by filtration, and 250 g of methanol was dropwise added to the resultant toluene solution to precipitate a crystal.

The crystal was separated by filtration, and was dried to obtain 8.7 g of a treated product (yield 87%). The treated product thus obtained had a purity of 99.4% according to purity analysis carried out by using a high performance liquid chromatography (HPLC-6A, manufactured by Shimadzu Corporation).

A photoconductor was prepared by using the above treated product thus obtained in the same manner as in Example 9, and its electrophotographic performances were evaluated in the same manner as above.

Example 10

The following amine compound (charge-transporting material No. 10) was used in place of the charge-transporting material No. 9 used in Example 9, and was treated in the same manner as in Example 9 to obtain 8.4 g of a treated product (yield 84%).

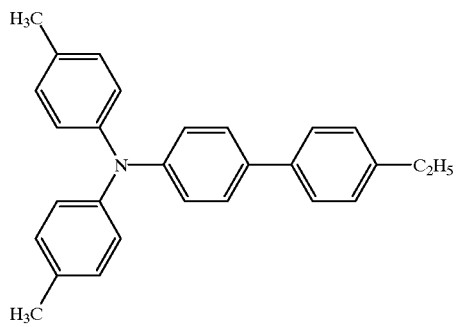

The treated product thus obtained had a purity of 99.6% according to purity analysis carried out in the same manner as above.

A photoconductor was prepared by using the above obtained treated product in the same manner as in Example 9, and its electrophotographic performances were evaluated in the same manner as above.

α type oxotitanyl phthalocyanine (charge-generating material No. 3) was used as a charge-generating material in place of the charge-generating material No. 4 used in Example 9

Comparative Example 10

The amine compound (charge-transporting material No. 10) was treated in the same manner as in Comparative Example 9 to obtain 8.5 g of a treated product (yield 85%). The treated product thus obtained had a purity of 99.4% according to purity analysis carried out in the same manner as above.

A photoconductor was prepared by using the above obtained treated product in the same manner as in Example 10, and its electrophotographic performances were evaluated in the same manner as above.

Example 11

The following amine compound (charge-transporting material No. 11) was used in place of the charge-transporting material No. 9 used in Example 9, and was treated in the same manner as in Example 9 to obtain 8.4 g of a treated product (yield 84%).

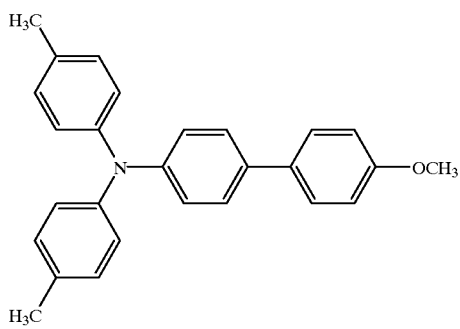

The treated product thus obtained had a purity of 99.4% according to purity analysis carried out in the same manner as above.

A photoconductor was prepared by using the above obtained treated product in the same manner as in Example 9, and its electrophotographic performances were evaluated in the same manner as above.

χ type metal free phthalocyanine (charge-generating material No. 1) was used as a charge-generating material in place of the charge-generating material No. 4 used in Example 9.

Comparative Example 11

The amine compound (charge-transporting material No. 11) was treated in the same manner as in Comparative Example 9 to obtain 8.4 g of a treated product (yield 84%). The treated product thus obtained had a purity of 99.3% according to purity analysis carried out in the same manner as above.

A photoconductor was prepared by using the above obtained treated product in the same manner as in Example 11, and its electrophotographic performances were evaluated in the same manner as above.

Example 12

The following amine compound (charge-transporting material No. 12) was used in place of the charge-transporting material No. 9 used in Example 9, and was treated in the same manner as in Example 9 to obtain 8.6 g of a treated product (yield 86%).

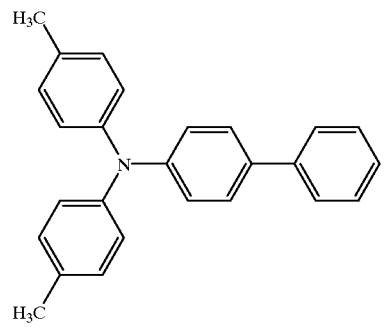

The treated product thus obtained had a purity of 99.8% according to purity analysis carried out in the same manner as above.

A photoconductor was prepared by using the above obtained treated product in the same manner as in Example 9, and its electrophotographic performances were evaluated in the same manner as above.

τ type metal free phthalocyanine (charge-generating material No. 2) was used as a charge-generating material in place of the charge-generating material No. 4 used in Example 9.

Comparative Example 12

The amine compound (charge-transporting material No. 12) was treated in the same manner as in Comparative Example 9 to obtain 8.5 g of a treated product (yield 85%). The treated product thus obtained had a purity of 99.7% according to purity analysis carried out in the same manner as above.

A photoconductor was prepared by using the above obtained treated product in the same manner as in Example 12, and its electrophotographic performances were evaluated in the same manner as above.

Example 13

The following benzidine compound (charge-transporting material No. 13) was used in place of the charge-transporting material No. 9 used in Example 9, and was treated in the same manner as in Example 9 to obtain 8.9 g of a treated product (yield 89%).

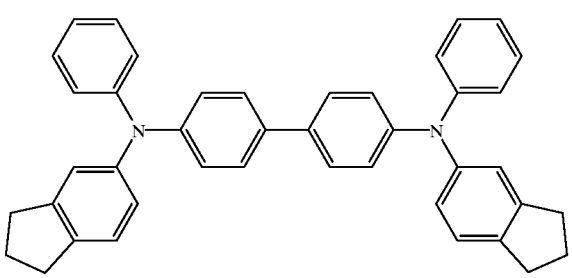

The treated product thus obtained had a purity of 99.7% according to purity analysis carried out in the same manner as above.

A photoconductor was prepared by using the above obtained treated product in the same manner as in Example 9, and its electrophotographic performances were evaluated in the same manner as above.

Comparative Example 13

The benzidine compound (charge-transporting material No. 13) was treated in the same manner as in Comparative Example 9 to obtain 8.9 g of a treated product (yield 89%). The treated product thus obtained had a purity of 99.5% according to purity analysis carried out in the same manner as above.

A photoconductor was prepared by using the above obtained treated product in the same manner as in Example 9, and its electrophotographic performances were evaluated in the same manner as above.

Example 14

Stilbene compound (charge-transporting material No. 14) as a charge-transporting material

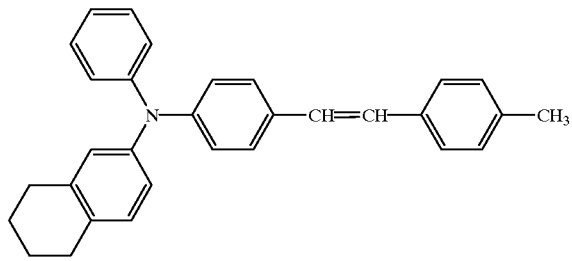

10 g of the above stilbene compound (charge-transporting material No. 14) wad dissolved in 60 g of toluene, and 10 g of activated clay T (manufactured by NIPPON KASSEIHAKUDO CO., LTD.) was added thereto, and the resultant mixture was stirred at 80° C. for 30 minutes, and the resultant mixture was subjected to separation by filtration, and 300 g of methanol was dropwise added to the resultant toluene solution to precipitate a crystal. The crystal thus precipitated was separated by filtration, and was dried to obtain 8.8 g of a treated product (yield 88%). The treated product thus obtained had a purity of 99.7% according to purity analysis carried out by using a high performance liquid chromatography (HPLC-6A, manufactured by Shimadzu Corporation).

A photoconductor was prepared by using the above obtained treated product in the following manner, and its electrophotographic performances were evaluated.

2.5 parts of alcohol-soluble nylon (Amilan CM-8000, manufactured by Toray Industries, Inc.) was added to 100 parts of a 1:1 (W/W) mixture solvent of methanol/n-butanol, and was completely dissolved therein. The resultant solution was coated on an aluminum surface of an aluminum-vapordeposited PET film as an electroconductive substrate by a wire bar, and was dried at 110° C. under normal pressure for 10 minutes to form an undercoat layer having a thickness of 0.2 $\mu$m.

On the other hand, 1.5 parts of a type oxotitanyl phthalocyanine (charge-generating material No. 3) as a charge-generating material was added to 50 parts of a 3% cyclohexanone solution of polyvinyl butyral resin (Eslex BL-S, manufactured by Sekisui Chemical Co., Ltd.), and the resultant mixture was subjected to milling in a pot mill for 24 hours. The dispersion thus obtained was coated on the above prepared undercoat layer by a wire bar, and was dried at 110° C. under normal pressure for 30 minutes to form a charge-generating layer having a thickness of 0.5 $\mu$m.

On the other hand, 1.5 parts of the above obtained treated product as a charge-transporting material was added to 12 parts of a 10% toluene solution of polycarbonate resin (IUPILON Z, manufactured by Mitsubishi Engineering Plastic K. K.), and was completely dissolved therein by applying ultrasonic wave. The solution thus obtained was coated on the above charge-generating layer by a wire bar, and was dried at 110° C. under normal pressure for 30 minutes and was further dried under reduced pressure for 2 hours to form a charge-transporting layer having a thickness of 22 $\mu$m, thus producing a photoconductor.

Electrophotographic performances of the photosensitive layer thus produced were evaluated by using an electrostatic copying paper tester (tradename "EPA-8100", manufactured by Kawaguchi Denki Seisakusho K. K.). Corona discharge of −6 kV was applied to the photosensitive layer in the dark to measure a charge potential V0 at this time. Thereafter, the photoconductor was exposed to 780 nm monocolor light of 1.0 $\mu$W/cm$^2$ to measure a half decay exposure amount E1/2 ($\mu$J/cm$^2$) and a residual potential Vr after continuous light irradiation for 5 seconds. The results are shown in the following Table 1-1.

Comparative Example 14

10 g of the stilbene compound (charge-transporting material No. 14) was dissolved in 60 g of toluene, and 10 g of activated clay T (manufactured by NIPPON KASSEIHAKUDO CO., LTD.) was added thereto, and the resultant mixture was stirred at 40° C. for 30 minutes, and the mixture was subjected to separation by filtration, and 300 g of methanol was dropwise added to the resultant toluene solution to precipitate a crystal. The crystal thus precipitated was separated by filtration, and was dried to obtain 8.9 g of a treated product (yield 89%). The treated product thus obtained had a purity of 99.6% according to purity analysis carried out by using a high performance liquid chromatography (HPLC-6A, manufactured by Shimadzu Corporation).

A photoconductor was prepared by using the above obtained treated product in the same manner as in Example 14, and its electrophotographic performances were evaluated.

TABLE 1-1

| Example and Comparative Example | V0 (−V) | Vr (−V) | E1/2 ($\mu$J/cm$^2$) |
|---|---|---|---|
| Example 1 | 701 | 3 | 0.34 |
| Comparative Example 1 | 692 | 24 | 0.39 |
| Example 2 | 651 | 1 | 0.29 |
| Comparative Example 2 | 679 | 12 | 0.33 |
| Example 3 | 609 | 0 | 0.21 |
| Comparative Example 3 | 582 | 5 | 0.26 |
| Example 4 | 650 | 3 | 0.29 |
| Comparative Example 4 | 656 | 8 | 0.30 |
| Example 5 | 638 | 1 | 0.26 |
| Comparative Example 5 | 601 | 19 | 0.30 |
| Example 6 | 595 | 0 | 0.19 |
| Comparative Example 6 | 634 | 14 | 0.26 |
| Example 7 | 790 | 19 | 0.40 |
| Comparative Example 7 | 752 | 59 | 0.56 |
| Example 8 | 655 | 0 | 0.27 |
| Comparative Example 8 | 612 | 3 | 0.28 |
| Example 9 | 622 | 0 | 0.15 |
| Comparative Example 9 | 514 | 32 | 0.21 |
| Example 10 | 666 | 0 | 0.24 |
| Comparative Example 10 | 631 | 28 | 0.38 |
| Example 11 | 800 | 14 | 0.43 |
| Comparative Example 11 | 771 | 63 | 0.60 |
| Example 12 | 649 | 3 | 0.37 |
| Comparative Example 12 | 678 | 39 | 0.58 |
| Example 13 | 587 | 0 | 0.22 |
| Comparative Example 13 | 580 | 3 | 0.24 |
| Example 14 | 591 | 0 | 0.28 |
| Comparative Example 14 | 603 | 3 | 0.29 |
| Example 18 | 620 | 8 | 0.33 |

TABLE 1-1-continued

| Example and Comparative Example | VO (−V) | Vr (−V) | E1/2 (μJ/cm²) |
|---|---|---|---|
| Comparative Example 18 | 584 | 11 | 0.35 |
| Example 19 | 614 | 0 | 0.30 |
| Comparative Example 19 | 610 | 9 | 0.32 |
| Example 20 | 592 | 0 | 0.28 |
| Comparative Example 20 | 593 | 4 | 0.28 |
| Example 21 | 542 | 1 | 0.22 |
| Comparative Example 21 | 548 | 8 | 0.23 |
| Example 22 | 561 | 0 | 0.21 |
| Comparative Example 22 | 570 | 33 | 0.40 |
| Example 23 | 504 | 0 | 0.29 |
| Comparative Example 23 | 490 | 3 | 0.29 |
| Comparative Example 24 | 693 | 21 | 0.38 |

Example 15
Stilbene compound (charge-transporting material No. 15) as a charge-transporting material

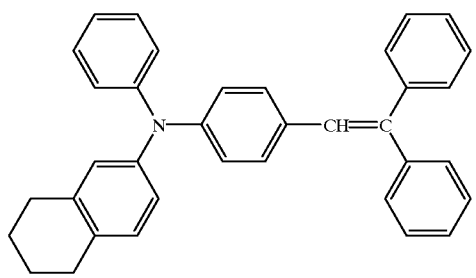

10 g of the above stilbene compound (charge-transporting material No. 15) was dissolved in 60 g of toluene, and 10 g of activated clay T (manufactured by NIPPON KASSEIHAKUDO CO., LTD.) was added thereto, and the resultant mixture was stirred at 80° C. for 30 minutes, and was subjected to separation by filtration, and 300 g of methanol was dropwise added to the resultant toluene solution to precipitate a crystal. The crystal thus precipitated was separated by filtration, and was dried to obtain 9.0 g of a treated product (yield 90%). The treated product thus obtained had a purity of 99.8% according to purity analysis carried out by using a high performance liquid chromatography (HPLC-6A, manufactured by Shimadzu Corporation).

A photoconductor was prepared by using the above obtained treated product in the following manner, and its electrophotographic performances were evaluated in the following manner.
Bisazo pigment (charge-generating material No. 5) as a charge-generating material

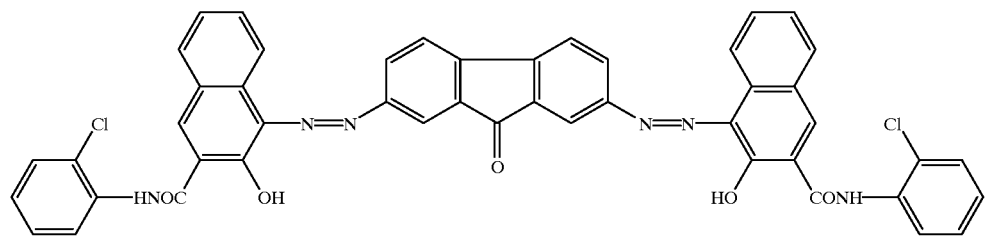

1.0 part of the above bisazo pigment (charge-generating material No. 5) and 8.6 parts of a 5% tetrahydrofuran solution of polyester resin (Viron 200, manufactured by Toyobo Co., Ltd.) were added to 83 parts of tetrahydrofuran, and the resultant mixture was placed in an agate pot containing agate balls, and was dispersed for 1 hour by rotating with a planetary grinder (manufactured by Fritsch Co.). The dispersion thus obtained was coated on an aluminum surface of an aluminum-vapordeposited PET film as an electroconductive substrate by a wire bar, and was dried at 60° C. under normal pressure for 2 hours and was further dried under reduced pressure for 2 hours to form a charge-generating layer having a thickness of 0.3 μm.

On the other hand, 1.5 parts of the above treated products as a charge-transporting material was added to 12 parts of a 10% toluene solution of polycarbonate resin (IUPILON Z, manufactured by Mitsubishi Engineering Plastic K. K.), and was completely dissolved therein by applying ultrasonic wave. The solution thus obtained was coated on the above charge-generating layer by a wire bar, and was dried at 110° C. under normal pressure for 30 minutes, and was further dried under reduced pressure for 2 hours to form a charge-transporting layer having a thickness of 22 μm, thus producing a photoconductor.

Electrophotographic performances of the above produced photosensitive layer were evaluated by using an electrostatic copying paper tester (tradename "EPA-8100" manufactured by Kawaguchi Denki Seisakusho K. K.). Corona discharge of −6 kV was applied to the photosensitive layer in the dark to measure a charge potential V0 at this time. The photosensitive layer was then exposed to white light of 1.0 lux to measure a half decay exposure amount E1/2 (lux·sec) and a residual potential Vr after continuous light irradiation for 5 seconds. The results are shown in the following Table 1-2.

TABLE 1-2

| Example and Comparative Example | VO (−V) | Vr (−V) | E1/2 (lux · sec) |
|---|---|---|---|
| Example 15 | 892 | 3 | 0.65 |
| Comparative Example 15 | 860 | 10 | 0.75 |
| Example 16 | 833 | 1 | 0.69 |
| Comparative Example 16 | 809 | 10 | 0.80 |
| Example 17 | 780 | 0 | 0.60 |
| Comparative Example 17 | 752 | 3 | 0.62 |

Comparative Example 15

10 g of the stilbene compound (charge-transporting material No. 15) was dissolved in 60 g of toluene, and 10 g of activated clay T (manufactured by NIPPON KASSEIHAKUDO CO., LTD.) was added thereto, and the resultant mixture was stirred at 40° C. for 30 minutes, and was subjected to separation by filtration, and 300 g of methanol was dropwise added to the resultant toluene solution to precipitate a crystal. The crystal thus precipitated was separated by filtration, and was dried to obtain 9.1 g of a treated product (yield 91%). The treated product thus obtained had a purity of 99.7% according to purity analysis carried out by using a high performance liquid chromatography (HPLC-6A, manufactured by Shimadzu Corporation).

A photoconductor was prepared by the above obtained treated product in the same manner as in Example 15, and its electrophotographic performances were measured in the same manner as above. The results are shown in the above Table 1-2.

Example 16

The following stilbene compound (charge-transporting material No. 16) was used as a charge-transporting material in place of the charge-transporting material No. 15 used in Example 15, and was treated in the same manner as in Example 15 to obtain 8.8 g of a treated product (yield 88%).

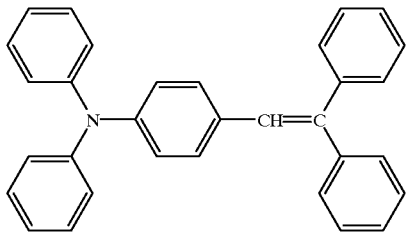

The above obtained treated product had a purity of 99.7% according to purity analysis carried out in the same manner as above.

A photoconductor was prepared by using the above obtained treated product in the same manner as in Example 15, and its electrophotographic performances were evaluated in the same manner as above. The results are shown in the above Table 1-2.

Comparative Example 16

The stilbene compound (charge-transporting material No. 16) was treated in the same manner as in Comparative Example 15 to obtain 9.0 g of a treated product (yield 90%). The treated product thus obtained had a purity of 99.6% according to purity analysis carried out in the same manner as above.

A photoconductor was prepared by using the above obtained treated product in the same manner as in Example 15, and its electrophotographic performances were evaluated in the same manner as above. The results are shown in the above Table 1-2.

Example 17

The following stilbene compound (charge-transporting material No. 17) was used as a charge-transporting material in place of the charge-transporting material No. 15 used in Example 15, and was treated in the same manner as in Example 15 to obtain 8.9 g of a treated product (yield 89%).

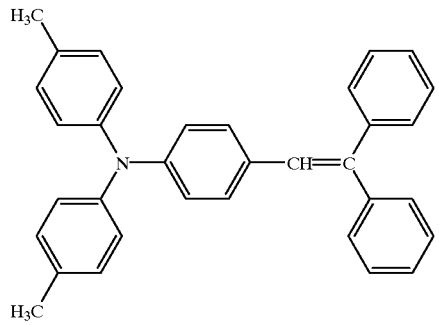

The treated product thus obtained had a purity of 99.6% according to purity analysis carried out in the same manner as above.

A photoconductor was prepared by using the above obtained treated product in the same manner as in Example 15, and its electrophotographic performances were evaluated in the same manner as above. The results are shown in the above Table 1-2.

Comparative Example 17

The stilbene compound (charge-transporting material No. 17) was treated in the same manner as in Comparative Example 15 to obtain 9.0 g of a treated product (yield 90%). The treated product thus obtained had a purity of 99.5% according to purity analysis carried out in the same manner as above.

A photoconductor was prepared by using the above obtained treated product in the same manner as in Example 15, and its electrophotographic performances were evaluated in the same manner as above. The results are shown in the above Table 1-2.

Example 18

Stilbene compound (charge-transporting material No. 18) as a charge-transporting material

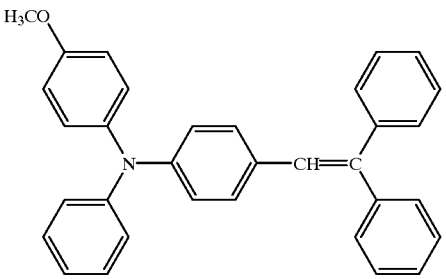

10 g of the above stilbene compound (charge-transporting material No. 18) was dissolved in 60 g of toluene, and 10 g of activated clay T (manufactured by NIPPON KASSEIHAKUDO CO., LTD.) was added thereto, and the resultant mixture was stirred at 80° C. for 30 minutes, and was subjected to separation by filtration, and 300 g of methanol was dropwise added to the resultant toluene solution to precipitate a crystal. The crystal thus precipitated was separated by filtration, and was dried to obtain 8.9 g of a treated product (yield 89%). The treated product thus obtained had a purity of 99.8% according to purity analysis carried out by using a high performance liquid chromatography (HPLC-6A, manufactured by Shimadzu Corporation).

A photoconductor was prepared by using the above obtained treated product in the following manner, and its electrophotographic performances were evaluated also in the following manner.

2.5 parts of alcohol-soluble nylon (Amilan CM-8000, manufactured by Toray Industries, Inc.) was completely dissolved in 100 parts of a 1:1 (W/W) mixture solvent of methanol/n-butanol. The resultant solution was coated on an aluminum surface of an aluminum-vapordeposited PET film as an electroconductive substrate by a wire bar, and was dried at 110° C. under normal pressure for 10 minutes to form an undercoat layer having a thickness of 0.2 μm.

On the other hand, 1.5 parts of a type oxotitanyl phthalocyanine (charge-generating material No. 3) as a charge-generating material was added to 50 parts of a 3% cyclohexanone solution of polyvinyl butyral resin (Eslex BL-S, manufactured by Sekisui Chemical Co., Ltd.), and the resultant mixture was subjected to milling in a pot mill for 24 hours. The dispersion thus obtained was coated on the above undercoat layer by a wire bar, and was dried at 110° C. under normal pressure for 30 minutes to form a charge-generating layer having a thickness of 0.5 μm.

On the other hand, 1.5 parts of the above obtained treated product as a charge-transporting material was added to 12 parts of a 10% toluene solution of polycarbonate resin (IUPILON Z, manufactured by Mitsubishi Engineering Plastic K. K.), and was completely dissolved therein by applying ultrasonic wave. The solution thus obtained was coated on the above charge-generating layer by a wire bar, and was dried at 110° C. under normal pressure for 30 minutes and was further dried under reduced pressure for 2 hours to form a charge-transporting layer having a thickness of 22 μm, thus producing a photoconductor.

Electrophotographic performances of the photoconductor thus produced were evaluated by using an electrostatic copying paper tester (tradename "EPA-8100" manufactured by Kawaguchi Denki Seisakusho K.K.). The photoconductor was then subjected to corona discharge of −6 kV in the dark to measure a charge potential V0 at this time. Thereafter, the photoconductor was exposed to 780 nm monocolor light of 1.0 μW/cm² to measure a half decay exposure amount E1/2 (μJ/cm²) and a residual potential Vr after continuous light irradiation for 5 seconds. The results are shown in the above Table 1-1.

Comparative Example 18

10 g of the above stilbene compound (charge-transporting material No. 18) was dissolved in 60 g of toluene, and 10 g of activated clay T (manufactured by NIPPON KASSEIHAKUDO CO., LTD.) was added thereto, and the resultant mixture was stirred at 40° C. for 30 minutes, and was subjected to separation by filtration, and 300 g of methanol was dropwise added to the resultant toluene solution to precipitate a crystal. The crystal thus precipitated was separated by filtration, and was dried to obtain 8.9 g of a treated product (yield 89%). The treated product thus obtained had a purity of 99.7% according to purity analysis carried out by using a high performance liquid chromatography (HPLC-6A, manufactured by Shimadzu Corporation).

A photoconductor was prepared by using the above obtained treated product in the same manner as in Example 18, and its electrophotographic performances were evaluated in the same manner as above.

Example 19

Hydrazone compound (charge-transporting material No. 19) as a charge-transporting material

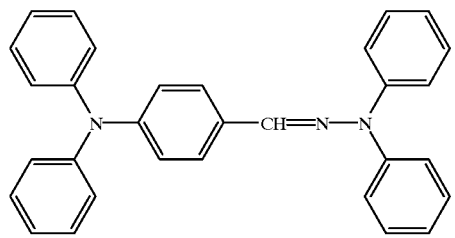

10 g of the above hydrazone compound (charge-transporting material No. 19) was dissolved in 70 g of toluene, and 10 g of Galleon Earth V₂ (manufactured by Mizusawa Industrial Chemicals, Ltd.), and the resultant mixture was stirred at 65° C. for 1 hour, and was subjected to separation by filtration, and 300 g of methanol was dropwise added to the resultant toluene solution to precipitate a crystal.

The crystal thus precipitated was separated by filtration, and was dried to obtain 9.0 g of a treated product (yield 90%). The treated product thus obtained had a purity of 99.9% according to purity analysis carried out by using a high performance liquid chromatography (HPLC-6A, manufactured by Shimadzu Corporation).

A photoconductor was prepared by using the above obtained treated product in the following manner, and its electrophotographic performances were evaluated also in the following manner.

2.5 parts of alcohol-soluble nylon (Amilan CM-8000, manufactured by Toray Industries, Inc.) was added to 100 parts of a 1:1 (W/W) mixture solvent of methanol/n-butanol, and was completely dissolved therein. The resultant solution was coated on an aluminum surface of an aluminum-vapordeposited PET film as an electroconductive substrate by a wire bar, and was dried at 110° C. under normal pressure for 10 minutes to form an undercoat layer having a thickness of 0.2 μm.

On the other hand, 1.5 parts of a type oxotitanyl phthalocyanine (charge-generating material No. 3) as a charge-generating material was added to 50 parts of a 3% cyclohexanone solution of polyvinyl butyral resin (Eslex BL-S, manufactured by Sekisui Chemical Co., Ltd.), and the resultant mixture was subjected to milling in a pot mill for 24 hours. The dispersion thus obtained was coated on the above undercoat layer by a wire bar, and was dried at 110° C. under normal pressure for 30 minutes to form a charge-generating layer having a thickness of 0.5 μm.

On the other hand, 1.5 parts of the above obtained treated product as a charge-transporting material was added to 12 parts of a 10% toluene solution of polycarbonate resin (IUPILON Z, manufactured by Mitsubishi Engineering Plastic K. K.), and was completely dissolved therein by applying ultrasonic wave. The resultant solution was coated on the above charge-generating layer by a wire bar, and was dried at 110° C. under normal pressure for 30 minutes and was further dried under reduced pressure for 2 hours to form a charge-transporting layer having a thickness of 22 μm, thus producing a photoconductor.

Electrophotographic performances of the photoconductor thus produced were evaluated by using an electrostatic copying paper tester (tradename "EPA-8100" manufactured by Kawaguchi Denki Seisakusho K.K.). The above photoconductor was subjected to corona discharge of −6 kV in the dark to measure a charge potential V0 at this time. The photoconductor was then exposed to 780 nm monocolor light of 1.0 μW/cm² to measure a half decay exposure amount E1/2 (μJ/cm²) and a residual potential Vr after continuous light irradiation for 5 seconds. The results are shown in the above Table 1-1.

Comparative Example 19

10 g of the hydrazone compound (charge-transporting material No. 19) was dissolved in 70 g of toluene, and 10 g of Galleon Earth V₂ (manufactured by Mizusawa Industrial Chemicals, Ltd.) was added thereto, and the resultant mixture was stirred at 40° C. for 1 hour, and was subjected to separation by filtration, and 300 g of methanol was dropwise added to the resultant toluene solution to precipitate a crystal.

The crystal thus precipitated was separated by filtration, and was dried to obtain 8.9 g of a treated product (yield 89%). The treated product thus obtained had a purity of 99.8% according to purity analysis s15 carried out by using a high performance liquid chromatography (HPLC-6A, manufactured by Shimadzu Corporation).

A photoconductor was prepared by using the above obtained treated product in the same manner as in Example 19, and its electrophotographic performances were evaluated in the same manner as above.

Example 20

The following hydrazone compound (charge-transporting material No. 20) was used in place of the charge-transporting material No. 19 used in Example 19, and was treated in the same manner as in Example 19 to obtain 9.1 g of a treated product (yield 91%).

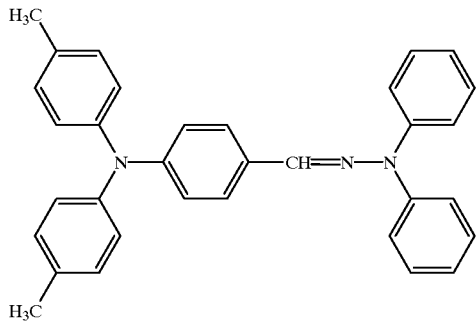

The treated product thus obtained had a purity of 99.7% according to purity analysis carried out in the same manner as above.

A photoconductor was prepared by using the above obtained treated product in the same manner as in Example 19, and its electrophotographic performances were evaluated in the same manner as above.

Comparative Example 20

The hydrazone compound (charge-transporting material No. 20) was treated in the same manner as in Comparative Example 19 to obtain 9.0 g of a treated product (yield 90%). The treated product thus obtained had a purity of 99.6% according to purity analysis carried out in the same manner as above.

A photoconductor was prepared by using the above obtained treated product in the same manner as in Example 19, and its electrophotographic performances were evaluated.

Example 21

Amine compound (charge-transporting material No. 21) as a charge-transporting material

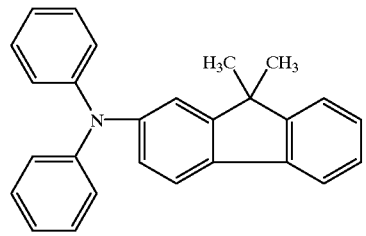

10 g of the above amine compound (charge-transporting material No. 21) was dissolved in 60 g of toluene, and 10 g of activated clay "Kyou" (manufactured by NIPPON KASSEIHAKUDO CO., LTD.) was added thereto, and the resultant mixture was stirred at 90° C. for 1 hour, and was subjected to separation by filtration, and 200 g of methanol was dropwise added to the resultant toluene solution to precipitate a crystal. The crystal thus precipitated was separated by filtration and was dried to obtain 7.9 g of a treated product (yield 79%). The treated product thus obtained had a purity of 99.8% according to purity analysis carried out by using a high performance liquid chromatography (HPLC-6A, manufactured by Shimadzu Corporation).

A photoconductor was prepared by using the above obtained treated product in the following manner, and its electrophotographic performances were evaluated also in the following manner.

2.5 parts of alcohol-soluble nylon (Amilan CM-8000, manufactured by Toray Industries, Inc.) was added to 100 parts of a 1:1 (W/W) mixture solvent of methanol/n-butanol, and was completely dissolved therein. The resultant solution was coated on an aluminum surface of an aluminum-vapordeposited PET film as an electroconductive substrate by a wire bar, and was dried at 110° C. under normal pressure for 10 minutes to form an undercoat layer having a thickness of 0.2 μm.

On the other hand, 1.5 parts of y type oxotitanyl phthalocyanine (charge-generating material No. 3) as a charge-generating material was added to 50 parts of a 3% cyclohexanone solution of polyvinyl butyral resin (Eslex BL-S, manufactured by Sekisui Chemical Co., Ltd.), and the resultant mixture was subjected to milling in a pot mill for 24 hours. The dispersion thus obtained was coated on the above undercoat layer by a wire bar, and was dried at 110° C. under normal pressure for 30 minutes to form a charge-generating layer having a thickness of 0.5 μm On the other hand, 1.5 parts of the above obtained treated product as a charge-transporting material was added to 12 parts of a 10% toluene solution of polycarbonate resin (IUPILON Z, manufactured by Mitsubishi Engineering Plastic K. K.), and was completely dissolved by applying ultrasonic wave. The resultant solution was coated on the above charge-generating layer by a wire bar, and was dried at 110° C. under normal pressure for 30 minutes and was further dried under reduced pressure for 2 hours to form a charge-transporting layer having a thickness of 22 μm, thus producing a photoconductor.

Electrophotographic performances of the photoconductor thus produced were evaluated by using an electrostatic copying paper tester (tradename "EPA-8100" manufactured by Kawaguchi Denki Seisakusho K.K.). Corona discharge of ~6 kV was applied to the photoconductor in the dark to measure a charge potential V0 at this time. Thereafter, the photoconductor was exposed to 780 nm monocolor light of 1.0 µW/cm² to measure a half decay exposure amount E1/2 (µJ/cm²) and a residual potential Vr after continuous light irradiation for 5 seconds. The results are shown in the above Table 1-1.

Comparative Example 21

10 g of the amine compound (charge-transporting material No. 21) was dissolved in 60 g of toluene, and 10 g of activated clay "Kyou" was added thereto, and the resultant mixture was stirred at 50° C. for 1 hour, and was subjected to separation by filtration, and 200 g of methanol was dropwise added to the resultant toluene solution to precipitate a crystal. The crystal thus precipitated was separated by filtration and was dried to obtain 8.0 g of a treated product (yield 80%). The treated product thus obtained had a purity of 99.7% according to purity analysis carried out by using a high performance liquid chromatography (HPLC-6A, manufactured by Shimadzu Corporation).

A photoconductor was prepared by using the above obtained treated product in the same manner as in Example 21, and its electrophotographic performances were evaluated in the same manner as above.

Example 22

The following amine compound (charge-transporting material No. 22) was used in place of the charge-transporting material No. 21 used in Example 21, and was treated in the same manner as in Example 21 to obtain 8.0 g of a treated product (yield 80%).

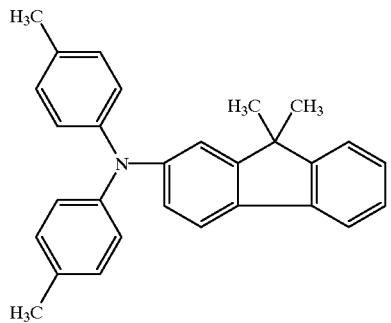

The treated product thus obtained had a purity of 99.6% according to purity analysis carried out in the same manner as above.

A photoconductor was prepared by using the above obtained treated product in the same manner as in Example 21, and its electrophotographic performances were evaluated in the same manner as above.

Comparative Example 22

The amine compound (charge-transporting material No. 22) was treated in the same manner as in Comparative Example 21 to obtain 8.1 g of a treated product (yield 81%). The treated product thus obtained had a purity of 99.4% according to purity analysis carried out in the same manner as above.

A photoconductor was prepared by using the above obtained treated product in the same manner as in Example 21, and its electrophotographic performances were evaluated in the same manner as above.

Example 23

The following amine compound (charge-transporting material No. 23) was used in place of the charge-transporting material No. 21 used in Example 21, and was treated in the same manner as in Example 21 to obtain 7.9 g of a treated product (yield 79%).

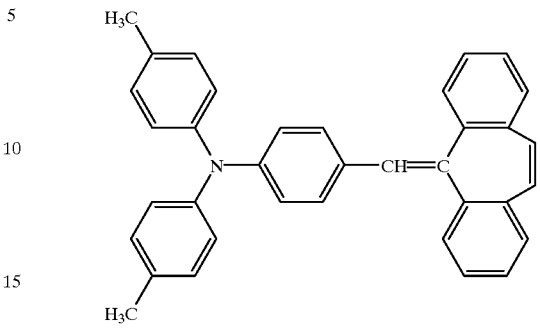

The treated product thus obtained had a purity of 99.7% according to purity analysis carried out in the same manner as above.

A photoconductor was prepared by using the above obtained treated product in the same manner as in Example 21, and its electrophotographic performances were evaluated in the same manner as above.

α type oxotitanyl phthalocyanine (charge-generating material No. 3) was used as a charge-generating material in place of the charge-generating material No. 4 used in Example 21.

Comparative Example 23

The amine compound (charge-transporting material No. 23) was treated in the same manner as in Comparative Example 21 to obtain 7.9 g of a treated product (yield 79%). The treated product thus obtained had a purity of 99.6% according to purity analysis carried out in the same manner as above.

A photoconductor was prepared by using the above obtained treated product in the same manner as in Example 23, and its electrophotographic performances were evaluated in the same manner as above.

Comparative Example 24

10 g of the above benzidine compound (charge-transporting material No. 1) was dissolved in 60 g of toluene, and 10 g of activated clay "Kyou" (manufactured by NIPPON KASSEIHAKUDO CO., LTD.) was added thereto, and the resultant mixture was stirred at 50° C. for 1 hour, and was subjected to separation by filtration, and 240 g of methanol was dropwise added to the resultant toluene solution to precipitate a crystal. The crystal thus precipitated was separated by filtration, and was dried to obtain 7.9 g of a treated product (yield 79%). The treated product thus obtained had a purity of 99.6% according to purity analysis carried out by using a high performance liquid chromatography (HPLC-6A, manufactured by Shimadzu Corporation).

A photoconductor was prepared by using the above obtained treated product in the same manner as in Example 1, and its electrophotographic performances were evaluated in the same manner as above.

As evident from the above evaluation results of electrophotographic performances, a photoconductor prepared by using a charge-transporting material treated with activated clay by heating at a temperature of at least 65° C. provides a higher sensitivity and a lower residual potential as compared with a photoconductor prepared by using a charge-transporting material treated at a low temperature. Thus, it is proved that the purification method of the present invention achieves a great effect.

According to the purification method of the present invention, such impurities as to cause unfavorable electric properties can be effectively removed by treating a charge-transporting material with activated clay by heating at a temperature of 65 to 200° C. By employing an improved excellent material produced by this treatment can provide a charge-transporting material having a high sensitivity and a low residual potential. Also, in the same manner, the purification method of the present invention can be widely applied to electronic item materials which require a high sensitivity. Also, by applying the purification method of the present invention to an intermediate stage, an excellent electronic item material can be provided.

What is claimed is:

1. A method for purifying an electronic item material, which comprises:

dissolving an electronic item material or its intermediate product in an organic solvent and contacting the solution with activated clay at a temperature of 80° C. to 130° C.

2. The method according to claim 1, wherein the electronic item material is an electrophotographic photoconductor.

3. The method according to claim 1, wherein the electronic item material is an organic electroluminescent device.

4. The method according to claim 1, wherein the electronic item material is a charge-transporting material.

5. A method for producing a charge-transporting material comprising:

dissolving a charge transporting material or its intermediate product in an organic solvent and contacting the solution with activated clay at a temperature ranging from 80° C. to 130° C.

6. The method of claim 5, comprising dissolving a charge-transporting material which is an arylamine derivative.

7. The method of claim 5, comprising dissolving a transporting-transporting material which is a benzidine derivative.

8. The method of claim 5, comprising dissolving a transporting-transporting material which is a hydrozone derivative.

9. The method of claim 5, comprising dissolving a transporting-transporting material which is a stilbene derivative.

10. The method of claim 5, wherein the solvent is an aliphatic hydrocarbon.

11. The method of claim 5, wherein the solvent is an aromatic hydrocarbon.

12. The method of claim 5, wherein the solvent is at least one member selected from the group consisting of toluene, o-xylene, m-xylene, p-xylene, o-cymene, p-cymene, anisole, n-hexane, n-heptane, n-octane, n-decane, n-dodecane, 2,3-dimethylhexane, 2-methylheptane, 2-methylhexane, 3-methylhexane, ethylxylene, ethyltoluene, ethylanisole, and dimethylheptane.

13. The method of claim 5, wherein the activated clay has a surface area of at least 150 $m^2/g$, an acidity of 10 to 30 m.e./100 g, and contains 70–85% $SiO_2$ and 6–15% $Al_3O_3$.

* * * * *